(12) United States Patent
Himmi et al.

(10) Patent No.: US 7,733,503 B2
(45) Date of Patent: Jun. 8, 2010

(54) METHOD AND SYSTEM FOR OPTICAL MEASUREMENT OF THE SHAPE OF AN ARTICLE

(75) Inventors: Mikko Himmi, Espoo (FI); Mikko Järvi, Helsinki (FI); Antti Knuuttila, Klaukkala (FI)

(73) Assignee: Oy Mapvision Ltd., Espoo (FI)

( * ) Notice: Subject to any disclaimer, the term of this patent is extended or adjusted under 35 U.S.C. 154(b) by 283 days.

(21) Appl. No.: 11/667,137

(22) PCT Filed: Nov. 21, 2005

(86) PCT No.: PCT/FI2005/000493

§ 371 (c)(1),
(2), (4) Date: Feb. 27, 2008

(87) PCT Pub. No.: WO2006/058954

PCT Pub. Date: Jun. 8, 2006

(65) Prior Publication Data

US 2009/0009774 A1    Jan. 8, 2009

(30) Foreign Application Priority Data

Nov. 30, 2004    (FI)    .................................. 20041545

(51) Int. Cl.
*G01B 11/24*    (2006.01)
(52) U.S. Cl. ...................................................... 356/602
(58) Field of Classification Search .................. None
See application file for complete search history.

(56) References Cited

U.S. PATENT DOCUMENTS

| 4,802,759 A | 2/1989 | Matsumoto et al. |
| 5,128,550 A | 7/1992 | Erbeck |
| 5,680,217 A | 10/1997 | Yli-Vakkuri |

FOREIGN PATENT DOCUMENTS

| EP | 0 747 664 A | 12/1996 |
| JP | 03-293506 | 12/1991 |

*Primary Examiner*—Gregory J Toatley, Jr.
*Assistant Examiner*—Amanda H Merlino
(74) *Attorney, Agent, or Firm*—Frommer Lawrence & Haug LLP; Ronald R. Santucci

(57) ABSTRACT

The present invention relates to a method and system for measuring articles made of a material that is difficult to measure, such as glass. In the system, an elastic film (19) is arranged on top of an article (110). A number of measurement points have been arranged on the film that are imaged using a machine vision system. The location of the measurement points imaged are calculated with respect to one another, and based on this, the shape of the article can be measured.

17 Claims, 4 Drawing Sheets

METHOD AND SYSTEM FOR OPTICAL MEASUREMENT OF THE SHAPE OF AN ARTICLE

This application is a 371 of PCT/FI2005/000493 filed on Nov. 21, 2005, published on Jun. 8, 2006 under publication number WO 2006/058954 A1 and claims priority benefits of Finnish Patent Application No. 20041545 filed Nov. 30, 2004, the disclosure of which is hereby incorporated by reference.

FIELD OF THE INVENTION

The present invention relates to machine vision systems and measurement of articles in quality control. In particular, the invention relates to the measurement of mirror-like and transparent articles that are difficult to measure.

BACKGROUND OF THE INVENTION

The present invention relates to machine vision systems and measurement of articles in quality control. In particular, the invention relates to the measurement of surfaces that are difficult to measure, including mirror and glass surfaces. Surfaces of this kind include automotive glasses that reflect light very poorly.

Conventional photogrammetric machine vision systems measure an object being viewed by focusing on them light spots or stripes and by taking images of the object using several cameras. The light pattern to be illuminated forms the object to be measured. The illumination apparatus can also consist of a number of illuminators or of a projector that reflects stripe patterns, enabling one to illuminate and measure several target spots simultaneously. The number of spots being illuminated can be increased by providing more illuminators, but this adds to the physical size of the illumination apparatus. An illumination apparatus alone will not often suffice to illuminate an entire article, instead the lights of an illuminator are often projected onto the desired location by projecting by means of a mirror. A number of cameras are used to take images of the measurement object illuminated by an illumination apparatus; and the locations of the spots are calculated using a central processing unit connected to the system.

The method referred to above is well suited for materials that reflect light. Instead, the method is poorly suited, for example, for the measurement of glass and plastic surfaces, particularly automotive glasses, which are bent in shape, because a regular laser light is not reflected from a glass surface in a manner allowing it to be imaged using cameras. In the case of automotive glasses, the measurement is particularly important also because of the fact that even small manufacturing defects can prevent installation of the glass in a car. Due to the importance of the problem, several different solutions have been developed to solve it.

In one solution, the piece of glass being measured is painted with a paint that reflects light better. Thereafter, the article can be measured using conventional photogrammetric machine vision systems. This method has the disadvantage of being expensive because prior to painting, the glass shall be cooled and washed right after the painting. Using an additional washing machine makes the production line more complicated and more expensive at the same time. In a version that has been further developed from this one, instead of paint, steam can be used that is condensed on the glass surface and need not be washed away. A disadvantage of this method is that the glass must be cooled so as to be so cold that steam is condensed on the glass surface.

In addition to conventional machine vision systems, specific machine vision systems for measuring glass have been developed. As in the manufacture of glass, a little of tin is left on the glass surface, which is due to the manufacturing method of glass, glass can be illuminated using an apparatus whose fluorescence in tin generates a visible measurement object. One such system has been described in publication U.S. Pat. No. 5,680,217, which discloses a method and system for measuring a bent glass sheet. In the method as shown in the publication, glass is imaged using an ultra violet laser with high intensity, allowing a sufficient amount of light to be reflected back from the glass to image it using, in other respects, however, conventional machine vision systems. The high price of an ultraviolet laser may also become a disadvantage of the solution presented. Furthermore, the high intensity to be used is risky, so due to work safety, the measurement arrangements must be implemented in an environment that is protected from light, because the intensities to be used can be harmful, for instance, to eyes. High intensities also involve problems with the camera devices to be used.

Conventionally, to measure the shape of glasses, mechanical sensors are used that are installed e.g. in a rack that supports the object being measured. In the case of an automotive windscreen, the windscreen is supported on the measurement rack by the same spots by which it would be fastened to the car. Thereafter, the measurement sensors are placed either beneath the glass or on top of it. Mechanical measuring instruments are complicated and slow. Being mechanical devices, they also are parts that wear and expose the glass being measured to measurement forces that can reduce the measurement accuracy. Further, a disadvantage of mechanical measuring instruments is that they are glass-specific, because each glass type must have their own measurement sensors in glass-specific measurement racks. One possibility to measure an article that is difficult to measure, that is to say a windscreen or a glass surface, is to measure and calculate the total reflection. This is, however, difficult because the objects being measured are of different shapes, making it nearly impossible to arrange the necessary total reflections.

Due to the above facts, there is an obvious need for a method and system that can be used to measure surfaces that are difficult to measure, such as glass, advantageously and efficiently.

OBJECTIVE OF THE INVENTION

The objective of the invention is to disclose a new type of method and system for measuring surfaces that are difficult to measure. One specific objective of the invention is to alleviate the aforementioned problems.

SUMMARY OF THE INVENTION

The present invention relates to a method and system for identifying the shape of articles that are difficult to measure. Factors that make it difficult to measure an article include a surface or a shape that reflects light poorly and would require moving the illumination apparatus. The system of the invention for measuring the shape of an article comprises an article being measured, a conventional fotogrammetric machine vision system comprising at least two cameras and a central processing unit for calculating the shape of the article based on the measurement results measured. Further, the system of the invention comprises an elastic film arranged on the surface of the article during measurement of the article.

In one embodiment of the invention, on the film surface there are arranged measurement points, for example, painted focusing marks. Focusing marks can consist, for example, of intersection points of lines of a regularly shaped grid, or of measurement points randomly placed on the film. If necessary, focusing marks can be made of a magnetic material that can be placed within the film. In one embodiment of the invention, to measure an article covered with a film, a conventional machine vision system is used in which the measurement points are illuminated onto the surface of the article using an illumination apparatus.

In one embodiment of the invention, the elastic film is arranged to form a closed space within which the cameras are arranged. In case the closed space is non-permeable to light, it can be provided with an illumination apparatus. The pressure in the closed space is controlled by means of inlet and outlet valves. Alternatively, the closed space has been so formed that it is not completely hermetic and its pressure is reduced due to leakages during measurement. In case the surface pressure caused to the article by the closed space turns out to be significant, it can be alleviated by placing, opposite to the article, a pressurized cushion supporting the article and functioning with the same pressure.

In one embodiment of the invention, the elastic film is disposable and is placed on the surface of the article prior to the measurement. Preferably, the film is easily removable. Further, instead of a film, if necessary, it is possible to use a net-like structure having bench marks attached thereto.

The present invention describes a simple method and system for measuring surfaces that are difficult to measure. These include glass pieces that reflect light poorly. The film of the invention that has been provided with measurement points is advantageous and enables one to eliminate the illumination apparatus from the system. Illumination apparatuses are costly and their placing difficult, in case the shapes of articles form shadow areas. Further in the case of glass, as the illumination apparatus, one shall use an UV laser which is both costly and hazardous. Thus, one advantage of the invention is that the laser illuminator is eliminated, the price of the system is reduced and work safety is improved.

Further, the present invention has the advantage of making the system faster. As there are a large number of measurement points arranged on the film, they need not be illuminated separately; instead they can be imaged immediately. Due to this, the system is made faster because the time necessary to move the illumination apparatus is eliminated.

Further, the present invention has the advantage that a baggy closed space is formed by the film that acts as a dust shield in spaces in which one must measure articles that are ground, or otherwise in a dusty environment.

Further, an advantage of the invention is that it is flexible, allowing it to be used in conjunction with conventional machine vision systems. Due to this, the system is advantageous to introduce into use because the one utilising an embodiment of the invention only needs to purchase the inventive part of the system of the invention while at the same time utilizing a system previously purchased.

LIST OF FIGURES

DETAILED DESCRIPTION OF THE INVENTION

Figure 1:
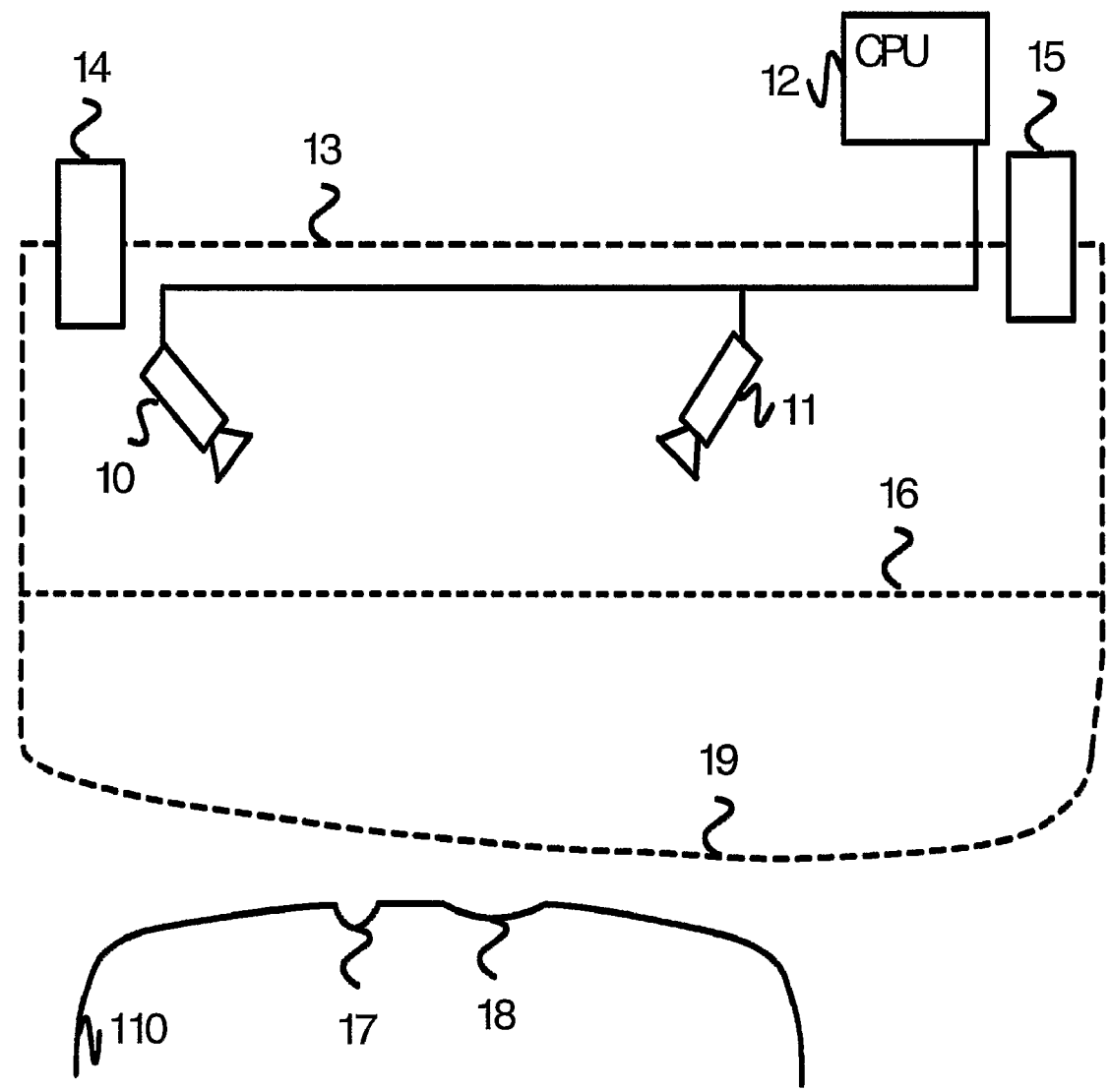
FIG. 1 represents one system in accordance with the invention shown in the initial state of preparing the measurement.
Figure 2:
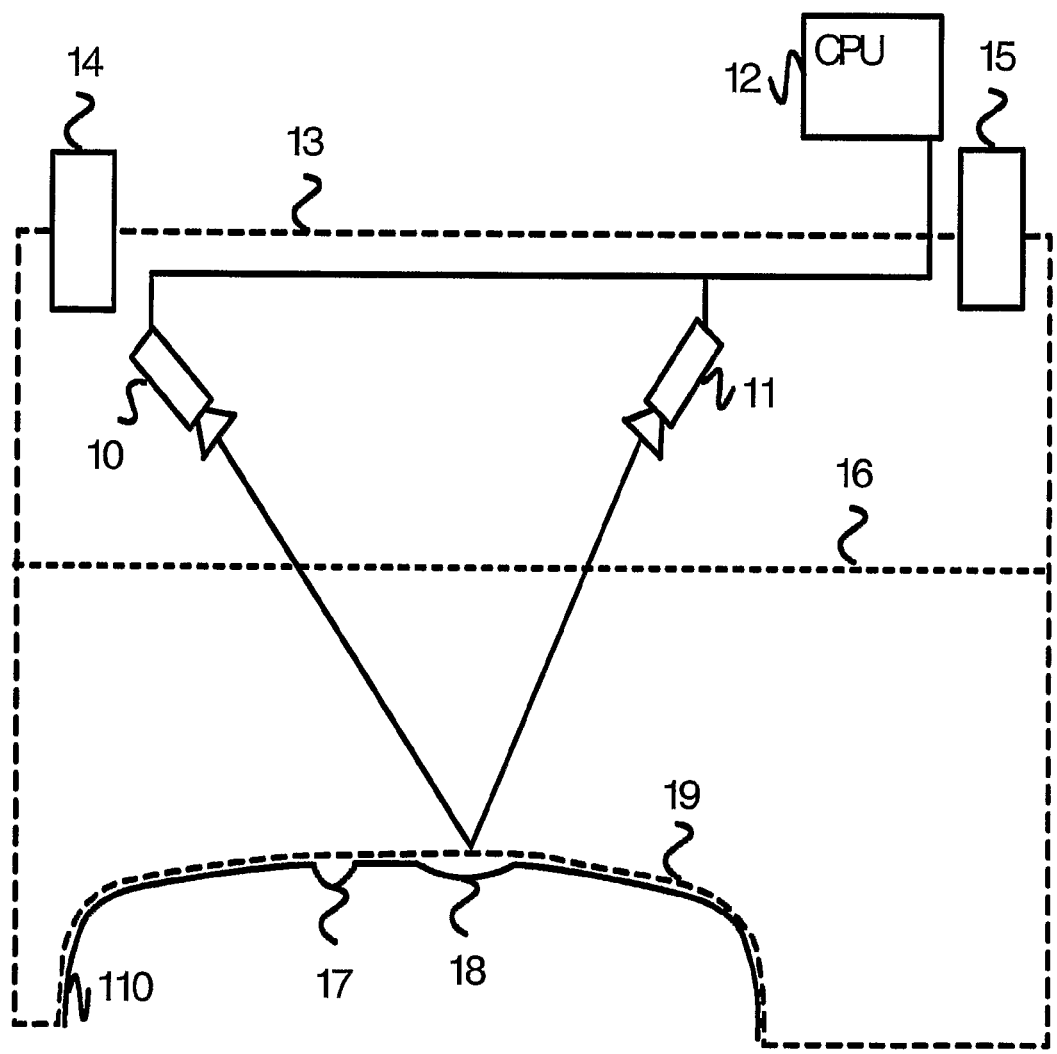
FIG. 2 represents one system in accordance with the invention shown in the intermediate phase of preparing the measurement.
Figure 3:
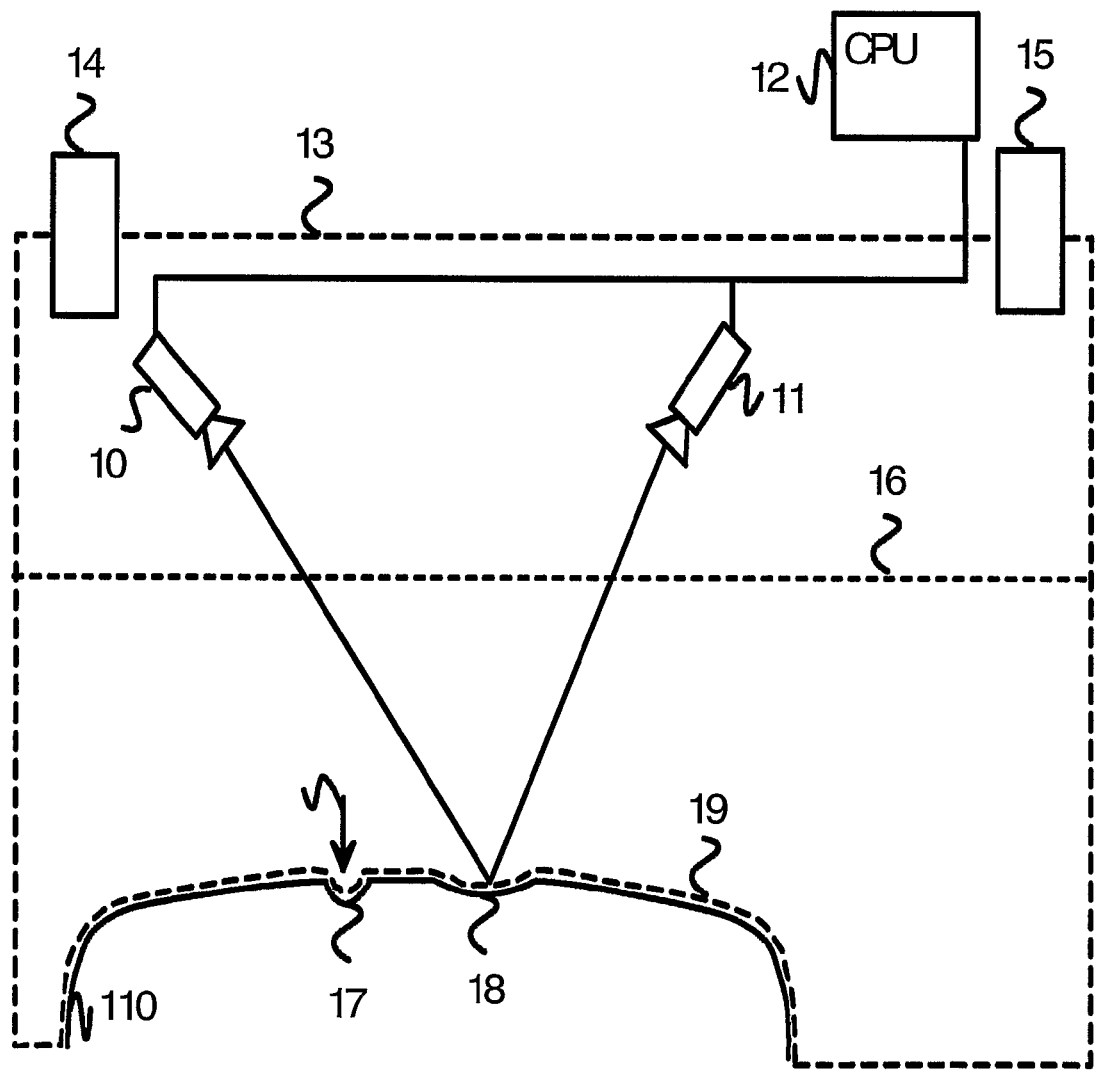
FIG. 3 represents one method in accordance with the invention shown in the measurement standby state.

The present invention relates to machine vision systems and measurement of articles in quality control. In particular, the invention relates to the measurement of surfaces that are difficult to measure, such as mirror and glass surfaces. Surfaces of this kind include automotive windscreens that reflect light very poorly. FIGS. 1-3 describe one preferred embodiment of the invention, as well as the phases of utilising the embodiment. The reference numerals used in FIGS. 1-3 correspond to each other.

The system as shown in FIGS. 1-3 includes at least two cameras 10 and 11, as well as a central processing unit arranged to calculate the actual measurement results from the views perceived by the cameras. As the camera and central processing unit part used in the system of the invention one can use a conventional machine vision system that is obvious to a person skilled in the art.

Further, the system comprises an article being measured 110, which is placed on a measurement support. All suitable measurement supports may be suitable for use as a measurement support, and are obvious to a person skilled in the art. For example in the case of a windscreen, the windscreen is placed on the measurement support using the same spots by which the windscreen is attached to the car. Due to this, the measurement support is selected based on the article being measured.

In FIGS. 1-3 depressions 17 and 18 represent examples of various defective shapes, intended to be perceived using the system of the invention. The shape of the defective depressions varies according to the manufacturing quality, and instead of the tiny depressions shown in the figure, they can be deformations occupying the entire article.

The present invention further comprises a film comprising of an upper part 13 and a lower part 19, as well as of a junction 16 for connecting the upper and lower part. For example, a zipper can act as a junction. In one embodiments of the invention, it is also possible to use just the lower part 19. The film material and colour can be selected according to need. In case the film is made of a material impermeable to light and both the upper and lower part are used in the embodiment, the inside of the film shall be provided with a general-purpose illuminator. To enable a fast measurement, a pattern with marks is made in the film. The pattern with marks can be, for example, a regularly shaped grid painted on the film surface, or a large number of randomly placed marking points. In one embodiment, the grid is formed of metal wires disposed within the film. The upper part 13 of the film can be provided with an inlet valve 14 and an outlet valve 15, which are used to control the amount of air within the film. However, the film need not be hermetic; instead small leakages, for example, in the junction 16 are permitted.

FIG. 1 illustrates a situation in which an article 110 has been placed on a measurement support to be measured. The measurement is started by putting down the lower part 19 of the film on top of the article, or by lifting the article to be in engagement with the film. The film has been placed in the measuring machine with its middle point being disposed lower than the edges. This can be arranged using, for example, side abutments that give support to the edges of the film, still allowing the middle point to hang freely.

FIG. 2 illustrates a situation in which the lower part 19 of the film has been put down on top of an article 110 being measured. From the figure it will be apparent that the lower part 19 of the film does not completely cover the article 110.

If the article was measured at this point with cameras 10 and 11, this would give an erroneous measurement result because the film will rectify the flaws 17 and 18 in the article.

FIG. 3 illustrates a final situation in which an article 110 is measured. The lower part 19 of the film is pressed against the surface of the article 110 by increasing the pressure in the space formed by the lower part 19 and upper part 13 of the film by pumping using an inlet valve 14. Preferably, the inlet valve 14 is used to pump air, but if necessary, also other gases can be used. The pressure formed in the space due to the pumping acts to attach the lower part 19 of the film to the surface of the article 110. From the viewpoint of the present invention, the selection of the film material is essential in that the film shall be of sufficient elasticity in order that it can be pressed against the surface of a desired article. The film shall be the more elastic, the smaller are the flaws one wishes to perceive.

A film of the aforementioned kind consisting of two parts is advantageous also due to the fact that in that case the necessary equipment can be wholly placed within the film, thereby protecting the equipment from dust.

In one embodiment of the invention, just the lower part of the film is used, making it necessary to press the film against the surface of an article being measured in a different manner. Alternative ways of pressing the article include static electricity, magnetism or use of a fan. However, it is substantial also in this embodiment that the film is of sufficient elasticity to be pressed against the surface of the article being measured.

Typically, in the system in accordance with the invention, there are focusing marks painted in the film, for example, in the form of a regularly shaped grid, enabling one to measure the intersections of the grid using a machine vision system. The shape of an article can be calculated from the measured locations of the intersections. No other location information is necessary to calculate the shape of the article. The film can also be manufactured to be transparent, enabling one to place the focusing marks within the film. Focusing marks placed within a film can be made, for example, of metal, enabling one to stretch the film over the surface of the article magnetically.

In one embodiment of the invention, an article is measured in a conventional manner by illuminating the spots with an illuminator of a machine vision system. This may be necessary if the film cannot be provided with measurement points. However, it is not preferred to use an illuminator, if there are a lot of spots to be measured because it takes time to move an illuminator. As the measurement quality is improved by using several spots, typically there is an attempt to measure as many spots as reasonably possible. The film of the present invention, provided with measurement points, can be used to measure a large number of spots without stopping, and the illumination apparatus need not be moved.

Figure 4:
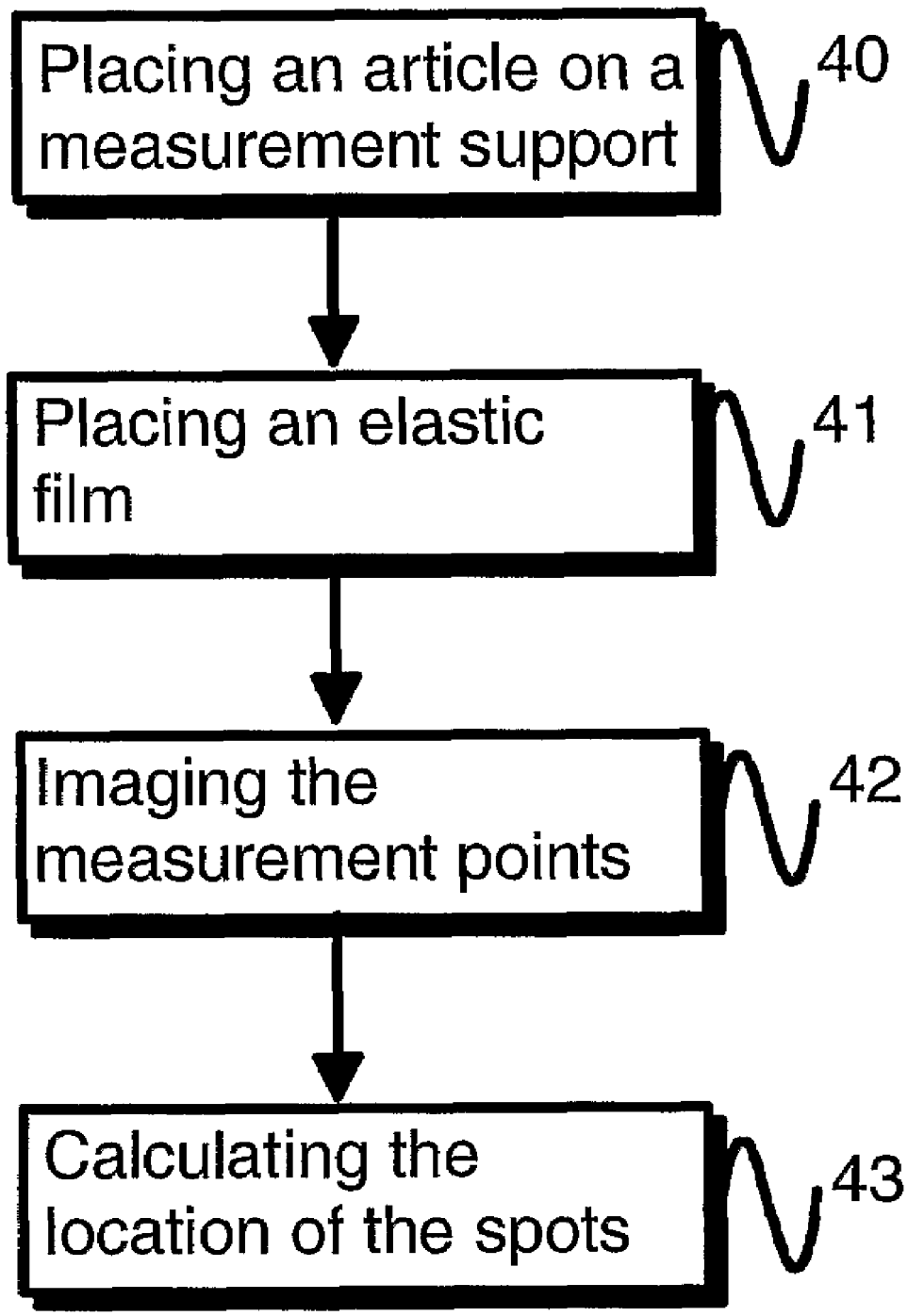
FIG. 4 represents one method in accordance with the invention.

FIG. 4 represents a method of the present invention in which an article is measured using a system in accordance with the present invention. The method of the invention is started by placing the article being measured on a measurement support, step 40. The measurement support can vary depending on the article being measured because articles typically impose physical requirements on how the articles are fastened.

An elastic film is placed on top of an article thus fastened, step 41. Preferably, the film is provided with a large number of measurement points. The film is placed on top of the article using, for example, air pressure, a fan or magnetism.

The film being placed, the measurement points arranged on the film are measured, step 42. The location of the points measured and the shape of the article are determined based on conventional machine vision methods, step 43.

The invention is not limited merely to the examples of its embodiments referred to above; instead many variations are possible within the scope of the inventive idea defined by the claims.

The invention claimed is:

1. A method for measuring the shape of an article, in which method at least two cameras take images of the article to determine the location of measurement points arranged on the surface of the article, wherein the method comprises the steps of: placing a film or a net on the surface of the article being measured to follow the contours of the surface of the article; measuring the measurement points arranged on the aforementioned film or net; and calculating the shape of the article based on the measurement.

2. The method as defined in claim 1, wherein the measurement points are painted on the surface of the aforementioned film or net.

3. The method as defined in claim 1, wherein the measurement points are arranged within the aforementioned film or net.

4. The method as defined in claim 1, wherein an illumination apparatus is used to illuminate the measurement points onto the surface of the aforementioned film or net.

5. The method as defined in claim 1, wherein the aforementioned film or net is placed on the surface of an article using pressure.

6. The method as defined in claim 1, wherein the aforementioned film or net is placed on the surface using static electricity.

7. The method as defined in claim 1, wherein the aforementioned film or net is placed on the surface of an article using magnetism.

8. A system for measuring the shape of an article, the system comprising:
   the article being measured; at least two cameras for measuring the aforementioned article; a film or net which is arranged on the article during measurement wherein measurement points are arranged on the surface of the aforementioned film or net; a central processing unit for calculating the shape of the aforementioned article based on the measurement.

9. The system as defined in claim 8, wherein the film or net is arranged to form a closed space.

10. The system as defined in claim 9, wherein the aforementioned cameras are arranged in the aforementioned closed space.

11. The system as defined in claim 9, wherein the system further comprises an inlet valve for increasing the pressure in the closed space.

12. The system as defined in claim 9, wherein the system further comprises an outlet valve for decreasing the pressure in the closed space.

13. The system as defined in claim 9, wherein the closed space is divided into two parts by junction means.

14. The system as defined in claim 8, wherein measurement points are arranged within the aforementioned film or net.

15. The system as defined in claim 8, wherein the system further comprises an illumination apparatus for illuminating the measurement points onto the surface of a film or net.

16. The system as defined in claim 8, wherein beneath the article being measured there is arranged a supporting cushion.

17. The system as defined in claim 8, wherein the aforementioned film is a film or net disposable and easily removable from the surface of the article being measured, the film or net being placed or injected on top of the article prior to the measurement.

* * * * *